Figure 1:
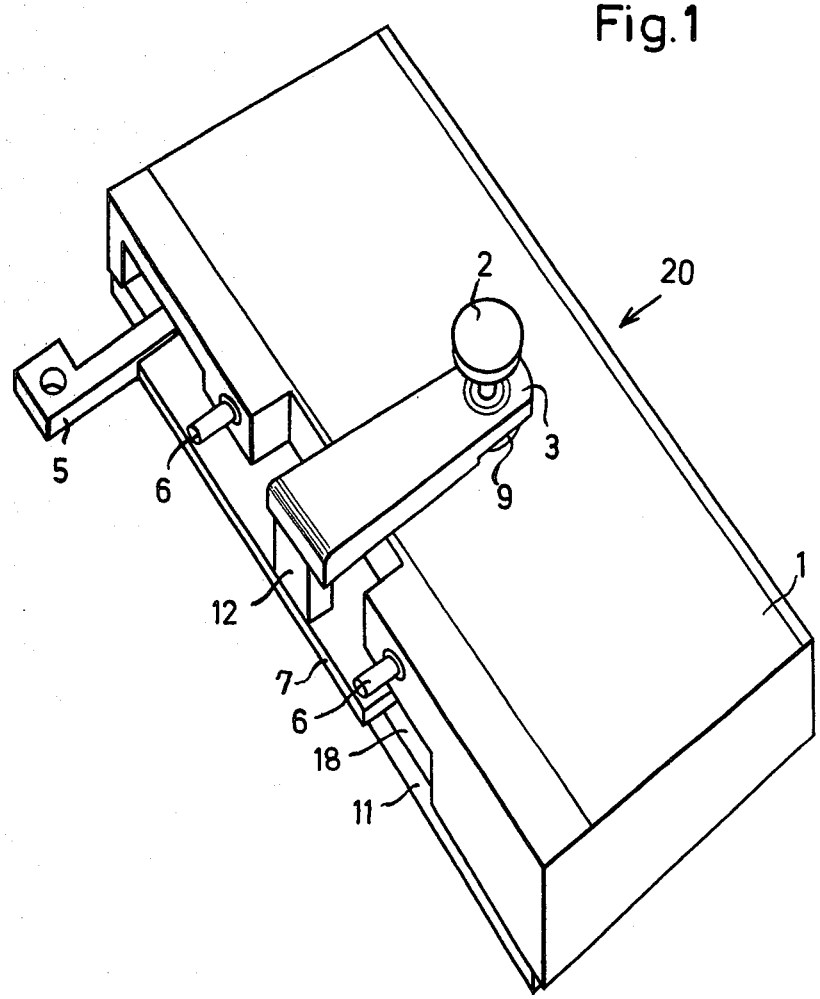

United States Patent [19]

Kutscherauer et al.

[11] 4,094,593
[45] June 13, 1978

[54] INSTRUMENT BASE FOR OPHTHALMOLOGICAL INSTRUMENTS

[75] Inventors: Andreas Kutscherauer, Oberkochen; Ortwin Müller, Konigsbronn, both of Germany

[73] Assignee: Carl Zeiss-Stiftung, Oberkochen, Germany

[21] Appl. No.: 719,811

[22] Filed: Sep. 1, 1976

[30] Foreign Application Priority Data

Sep. 16, 1975 Germany .............................. 7529211

[51] Int. Cl.$^2$ ................................................. A61B 3/00
[52] U.S. Cl. ................................ 351/38; 74/471 XY; 248/23
[58] Field of Search ...... 351/38; 74/471 XY, DIG. 2; 248/23, 429, 430

[56] References Cited

U.S. PATENT DOCUMENTS

| | | | |
|---|---|---|---|
| 2,940,357 | 6/1960 | Oswald | 351/38 |
| 3,463,579 | 8/1969 | Papritz | 351/38 |

OTHER PUBLICATIONS

R. Schön et al., *Jena Review*, No. 2, pp. 142–144, 12/1969.

*Primary Examiner*—Paul A. Sacher
*Attorney, Agent, or Firm*—Hopgood, Calimafde, Kalil, Blaustein & Lieberman

[57] ABSTRACT

A base for ophthalmological instruments includes a housing within which is mounted a guide plate to which an ophthalmological instrument may be attached. The guide plate extends through an opening in the side of the housing and is mounted on bearings which permit translational movement of the plate along coordinate axes x-y to thereby permit adjustment of the instrument as desired by the physician. The upper surface of the housing serves as a table and a control arm connected to the guide plate extends across the table. A control lever mounted in gimbals on the control arm is provided for fine adjustment of the guide plate. Means are provided for locking the guide plate in any position of adjustment.

5 Claims, 6 Drawing Figures

INSTRUMENT BASE FOR OPHTHALMOLOGICAL INSTRUMENTS

This invention relates to an instrument base for ophthalmological instruments.

When working with ophthalmological instruments, an exact geometrical adjustability of the instrument to the eye or eyes to be examined is required. When examining seated patients, movement of the instrument in two directions, i.e. on coordinate axes x-y, is of particular importance, as, for example, when adjusting an ophthalmological instrument from one eye to the other, or when examining the cornea of an eye. This capacity for translation of the instrument on coordinate axes x-y must be provided for every precision instrument.

Various forms of instrument bases for ophthalmological instruments are known. The known instrument bases are designed mainly to take account of the weight of the ophthalmological instrument mounted thereon and the requirements as to the mobility of the instrument. In the case of the known instrument bases, the guide elements for controlling movement along the x-y axes are arranged either above or below a platform which serves as table and support. When arranged above the platform, the guides are frequently integrated into the examining instrument. This arrangement of the guide elements has the disadvantage that a separate table is necessary for the mounting of the instrument, which is then, however, not available as a work table or a resting or support surface for the user, since practically the entire free surface of the mounting table below and around the instrument is taken up by the guide means itself.

In the known instrument bases in which the guide elements are arranged below the supporting table, the instrument is fastened to the upper surface of the table and the latter is moved for translation of the instrument along the x-y axes. This type of guidance, however, has the disadvantage that the user has difficulty when he desires to rest his arms on the movable platform during the examination.

It is an object of the present invention, therefore, to provide an instrument base for ophthalmological instruments in which the elements for the control and guiding of the movement are simple and convenient for the user to manipulate. Furthermore, the user is provided with a large work surface and a convenient and reliable support for his arms.

This object is achieved in accordance with the present invention in that the guide elements for movement of the ophthalmological instruments along the x-y axes are arranged within a hollow housing which remains stationary during the movement of the instrument, a guide plate being movably supported within the housing to provide for the movement of the instrument, and the upper surface of the housing being available as a stationary work table for the user.

Conveniently, on the side of the housing facing the patient, means are provided for attachment of a patient's headrest.

The guide plate which is movably supported within the housing is provided with means for attaching ophthalmological instruments thereto, and the plate is connected with a control arm extending across the work table for controlling the movements of the instrument.

While the coarse movements of the ophthalmological instrument, such as required, for example, for shifting from one eye to the other are effected by direct movement of the control arm, a hand control stick supported movably in the control arm is provided for the fine adjustment of the instrument during examination of an eye, the control stick being provided with a supporting and friction plate engaging the work table.

For many uses of the instrument base of the present invention, it is advantageous to install electric operating elements in the control arm.

Electromagnetic devices for braking of the movement of the instrument may suitably be provided. By means of these electromagnetic devices, the examining instrument can be fixed easily and precisely in position.

By attaching table legs or a column to the bottom of the housing, the instrument base can be made into a complete, stable instrument carrier. On the other hand, the housing can also be placed on any suitable table.

The advantages of the invention consist, in particular, in the fact that the user is provided with a large table surface as a work surface and as support for his arms, and that this table surface remains stationary during movements of the instrument. Another advantage resides in its compact modular concept of construction, which permits the attaching of table legs or a stand as well as different ophthalmological instruments and a patient's headrest to the instrument base.

Figure 2:
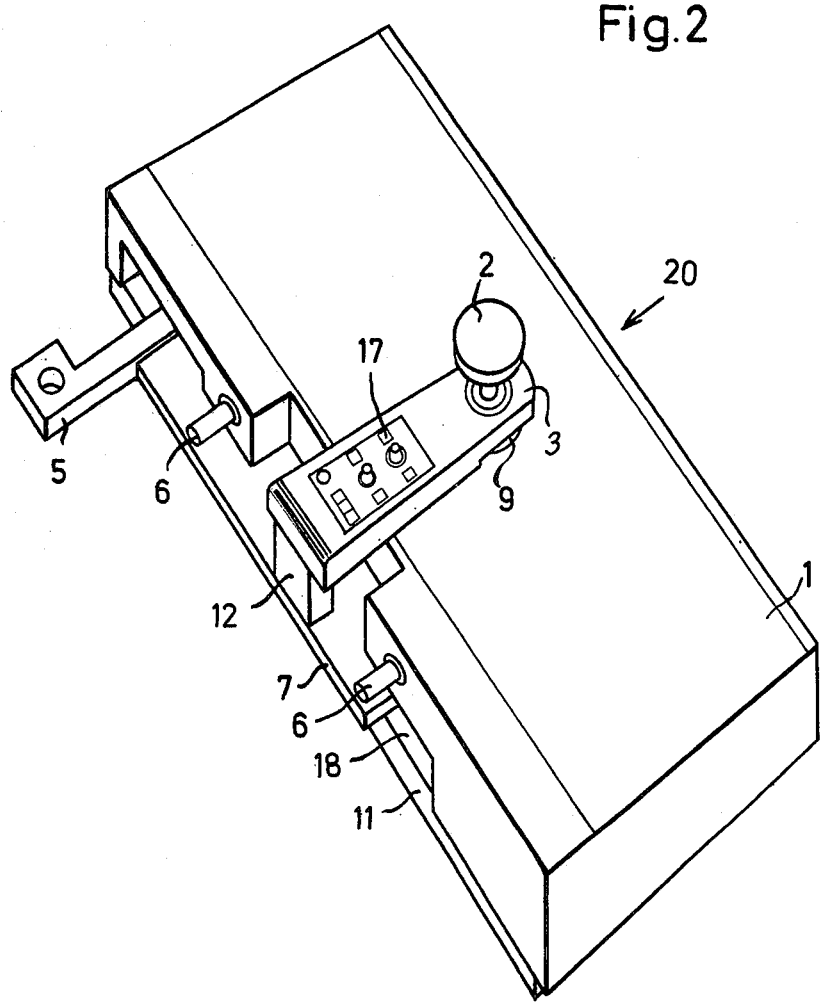
Figure 3:
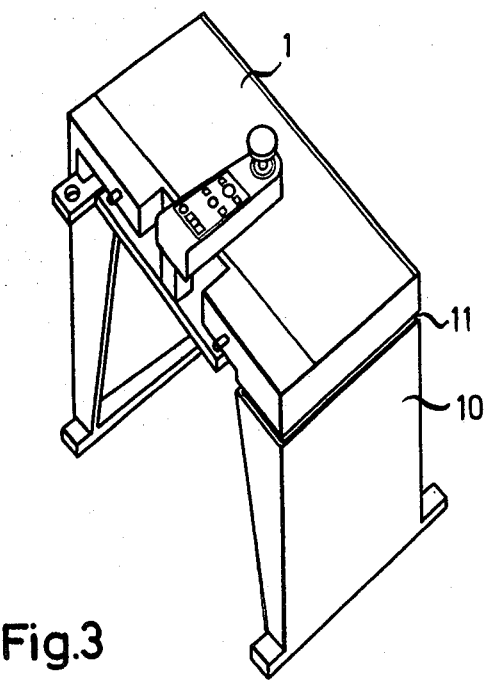
Figure 4:
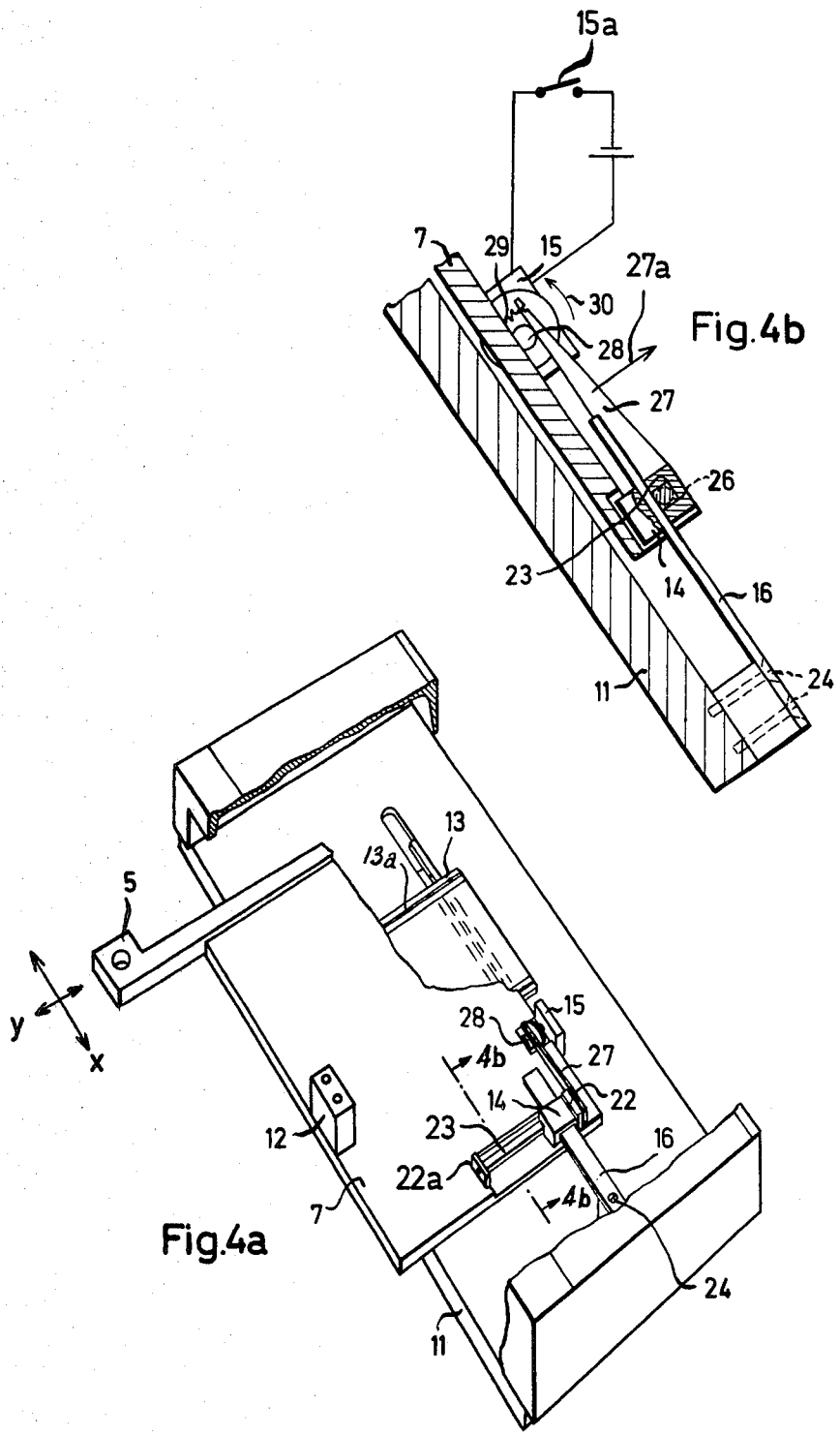
Figure 5:
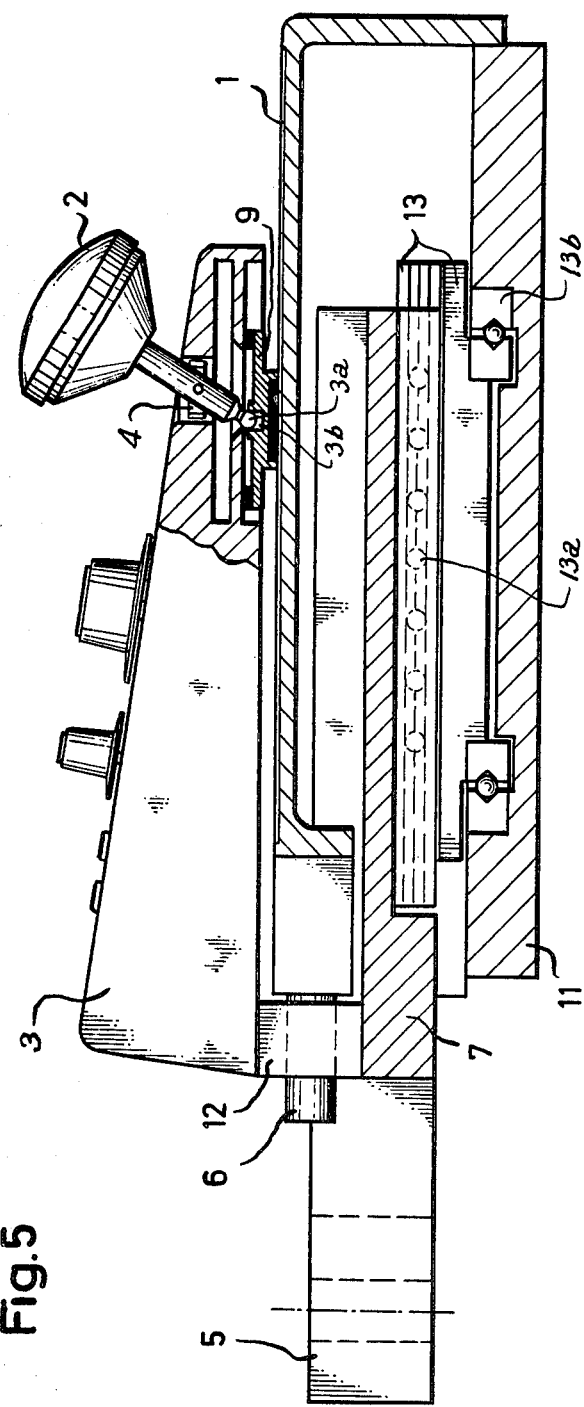

A preferred embodiment of the invention is shown in the accompanying drawings, in which:

FIG. 1 is a perspective view of the top of an instrument base embodying the invention, FIG. 2 is a perspective view of the top of a modified form of an instrument base embodying the invention, FIG. 3 is a perspective view of an instrument base embodying the invention mounted on table legs, FIG. 4a is a perspective view of the top of an instrument base, partly broken away to show means for braking and fixing the instrument movement, FIG. 4b is a section on the line 4b of FIG. 4a, and FIG. 5 is a longitudinal section through the instrument base including the control arm.

In the drawings, 20 designates generally a hollow instrument base housing having an upper surface 1 which serves as a table surface or tray, and as an arm support for the examining physician. A headrest (not shown) may be mounted on the housing 20 by means of pins 6. As shown in FIG. 3, table legs 10 may be secured to the bottom plate 11 of the housing in any suitable manner.

On the side of the housing 20 which faces the patient, the housing is provided with an opening 18 through which the guide plate 7 protrudes. The opening 18 is large enough to permit movement of the plate 7 on both of the coordinate axes x-y as hereinafter described. An arm 5 mounted on the plate 7 is provided for attachment to an ophthalmological instrument. The plate 7 is rigidly connected to a control arm 3 by a post 12 so that movement of the arm 3 in any direction as hereinafter described is transmitted to plate 7.

Plate 7 is mounted to slide forwardly and backwardly on the two part cross slide 13 on bearings 13a carried thereby, and the cross slide 13, in turn, is mounted to slide transversely on the bottom plate 11 of the housing on bearings 13b carried thereby. Thus, the plate 7 is capable of sliding movement in both longitudinal and transverse directions with respect to the housing. Fine adjustment in either direction may be controlled by a control lever 2 mounted on gimbals 4 in the control arm 3. The lower end of the lever 2 terminates in a ball 3a which extends into a socket 3b in a friction plate 9 which bears on the upper surface 1 of the housing. Thus, fine adjustment in any direction of the plate 7 and of the instrument carried thereby may be effected by suitable movement of the control lever 2. Coarse adjustment may be effected by direct movement of the control arm 3.

As illustrated in FIGS. 2 and 5, the control arm 3 may be provided with an electrical control panel 17 having suitable control switches for the control and operation of a microscope, for example, such as for motor control of vertical and horizontal movement of the microscope, for change of magnification, for adjustment of illumination, for the operation of camera shutters and flash discharges, and the like.

If desired, the control panel may also be provided with means to control the operation of a brake mechanism to hold the plate 7 in any desired position of adjustment. The said mechanism includes a lock member 14 having two slots extending therethrough at right angles to each other which are adapted to receive in sliding relation thereto a guide bar 16 rigidily mounted on the bottom plate 11 of the housing at 24 and extending transversely of the plate 7, and a guide bar 23 mounted on the plate 7 and extending longitudinally thereof.

The bar 23 is mounted for oscillation in bearing plates 22 and 22a which are fixed to the plate 7, with the rounded ends of the bar extending through apertures in the plates 22 and 22a. The portion of bar 23 between the rounded ends is rectangular in cross section as shown in FIGS. 4a and 4b and extends through a rectangular passage 26 in the lock 14. A lever arm 27 is fixed to the end of the bar 23 which extends through the bearing plate 22. With the lever arm 27 in the position shown in FIG. 4b, the plate 7 is in unlocked position since the bars 16 and 23 are free to slide in their respective slots in the lock 14 whenever the plate 7 is moved along either of the axes x or y. However, whenever the lever 27 is moved in clockwise direction as indicated by arrow 27a, the rotation of bar 23 produced thereby clamps both of the bars 16 and 23 in their respective slots in the lock 14, thus locking the plate 7 against movement in any direction.

The lever 27 is normally held in the unlocked position of FIG. 4b by a spring 29 but it may, of course, be lifted to locking position by hand. However, power actuated means are provided for lifting the lever 27 to locking position comprising a rotary magnet 15 mounted on plate 7 and connected to a suitable energy source through a circuit including a switch 15a. When the switch 15a is closed, the magnet is energized and the eccentric pin 28 of the magnet is moved in the direction indicated by arrow 30 to lift the lever 27 to locking position. It will be understood that the switch and circuit shown diagrammatically in FIG. 4b may be mounted in the control panel 17, if desired.

What is claimed is:

1. An instrument base for ophthalmological instruments comprising a hollow housing having an upper surface which serves as a table, said housing having means defining an opening in one side thereof, a guide plate within said housing and therefore beneath said table, at least a portion of said guide plate extending to the outside through the opening, means located within said housing for supporting said guide plate for movement along coordinate axes x-y, and a control arm connected to said guide plate and extending across a relatively small area of the upper surface of said table.

2. An instrument base as claimed in claim 1 in which said means for supporting said guide plate comprises a cross slide having bearings permitting movement of said guide plate thereon along an x axis, and in which said cross slide is mounted on bearings carried by said housing permitting movement of said cross slide and said guide plate along a y axis.

3. An instrument base as claimed in claim 1 including a control lever mounted in gimbals in said control arm, said lever extending into contact with said table.

4. An instrument base as claimed in claim 1 including means mounted on said guide plate for locking said guide plate against movement in any direction.

5. An instrument base as claimed in claim 4 in which said locking means comprises a lock member mounted on said guide plate and having two slots extending therethrough at right angles to each other, separate guide bars extending through said slots, one of said guide bars being fixed to said housing, and the other of said guide bars being mounted for oscillation on said guide plate, and means for locking said guide bars against movement in said slots.

* * * * *